United States Patent [19]

Boschung et al.

[11] 4,383,770

[45] May 17, 1983

[54] APPARATUS FOR DETERMINING THE FREEZING POINT OF A LIQUID ON OR FROM A ROAD SURFACE

[75] Inventors: Marcel Boschung, Schmitten; Walter Zehnder, St. Antoni, both of Switzerland

[73] Assignee: Boschung Mecatronic AG, Canton of Fribourg, Switzerland

[21] Appl. No.: 281,599

[22] Filed: Jul. 9, 1981

[51] Int. Cl.³ .............................................. G01N 25/04
[52] U.S. Cl. ..................................... 374/25; 364/557
[58] Field of Search ....................... 374/16, 17, 25, 26; 364/509, 557

[56] References Cited

U.S. PATENT DOCUMENTS

| | | | |
|---|---|---|---|
| 3,367,171 | 2/1968 | Kobayashi | 374/16 |
| 3,891,834 | 6/1975 | Warsinski | 364/509 |
| 4,222,044 | 9/1980 | Boschung . | |
| 4,304,119 | 12/1981 | Uchigaki | 374/25 |

OTHER PUBLICATIONS

Prager et al., "Freezing-Point Depression: New Method for Measuring Ultramicro Quantities of Fluid" in Science 10/63, vol. 142, pp. 237-239.

Der Chemielaborant, by Dr. Fritz Merten, Gebr. Janeke-Verlag, Hanover, 1966, p. 77.

Primary Examiner—Herbert Goldstein
Attorney, Agent, or Firm—Dann, Dorfman, Herrell and Skillman

[57] ABSTRACT

A portion of the test liquid is placed in the middle of a cooling plate having a central recess in which a thermometer probe is embedded in a heat-insulating material. Two Peltier elements disposed beneath the plate are connected in series and can be energized via a switch or a relay contact, thus chilling the portion of liquid. The probe may be connected to a voltage source and to an oscillograph which displays the voltage drop caused by the cooling liquid in the form of a curve. In another embodiment, the probe is series-connected to a constant-current source, and the voltage drop is amplified and supplied to an analog-to-digital converter connected to a microprocessor which both initiates the chilling operation and orders the A-D converter to sample the voltage and supply the equivalent digital value to the microprocessor itself. This order is repeated at regular intervals so that digital values corresponding to the solidification curve of the liquid can be stored in the microprocessor and evaluated there upon termination of the chilling process in order to determine the freezing point of the liquid, which temperature is then digitally displayed.

7 Claims, 9 Drawing Figures

APPARATUS FOR DETERMINING THE FREEZING POINT OF A LIQUID ON OR FROM A ROAD SURFACE

This invention relates to apparatus for determining the freezing points of liquids, particularly of liquids lying on or taken from roadways, of the type having a chilling device and a thermometer probe for measuring the temperature of the liquid.

If, during the chilling of a liquid, its temperature is continuously measured and plotted against the time, the temperature curve (so-called solidification or freezing-point curve) first slopes downward, then rises rapidly at a certain point, thereafter runs more or less horizontally for a time, and finally drops off again. This phenomenon is described, for example, in Der Chemielaborant, by Dr. Fritz Merten, Gebr. Jäneke-Verlag, Hanover, 1966, p. 77.

The chilling of the liquid to be examined and the plotting of the temperature curve, e.g., with the aid of recording apparatus, is no problem in the laboratory. It would naturally be possible to take samples of liquid found on a roadway to a laboratory and determine the freezing point of the samples there. However, until now there has been no simple apparatus for convenient and reliable on-the-spot determination of the freezing point of liquids found on a roadway, e.g., rainwater or melted snow in which a thawing agent such as salt is dissolved.

It is an object of this invention to provide improved apparatus by means of which the freezing point of liquid lying on or taken from a roadway can be reliably, simply, and quickly determined on the spot.

To this end, in the apparatus according to the present invention, of the type initially mentioned, a plate which is a good conductor of heat is heat-conductively connected to the chilling device, there is a recess in the central area of the plate, the thermometer probe is embedded in the recess by means of a heat-insulating material, and the thermometer probe is connected to an evaluating device for determining and displaying the freezing point of the liquid as a function of the temperature gradient.

The apparatus of the invention is suitable either for monitoring the freezing point of liquid on the roadway at one specific location or for mobile duty so that measurements can be carried out at any desired location.

Preferred embodiments of the invention will now be described in detail with reference to the accompanying drawings, in which.

Figure 1:
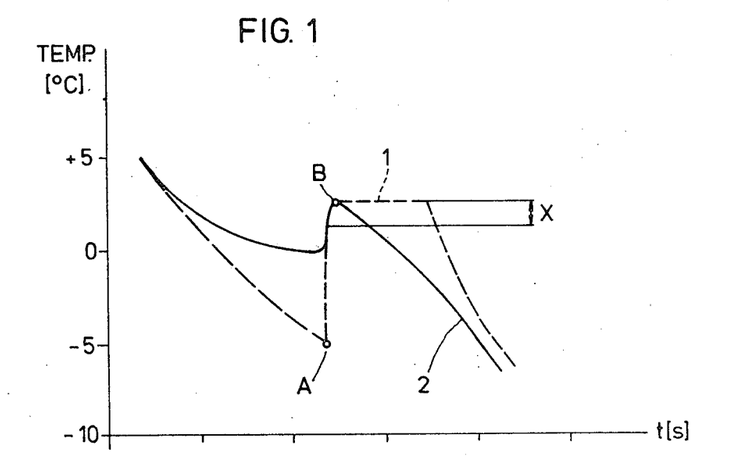
FIG. 1 is a graph showing in terms of time the temperature curve of a liquid chilled beyond its freezing or solidification point.

In the graph of FIG. 1, the time in seconds is plotted on the x-axis and the temperature in degrees Celsius on the y-axis. Broken-line curve 1 shows the shape of the temperature curve of a pure liquid, e.g., water, during the chilling process. As cooling increases, the temperature drops until it reaches a point A, whereupon there is a sudden rise in temperature to point B, following which the temperature remains constant for a certain time, then drops again. The marked drop in the temperature of the liquid below the solidification temperature is called undercooling. This is a lag in solidification attributable to delayed crystallization when no seed crystals are present. The solidification then remains totally constant for a short period of time only when the chilled liquid is completely pure. If the liquid is contaminated, the temperature curve takes the shape shown by solid-line curve 2.

Figure 2:
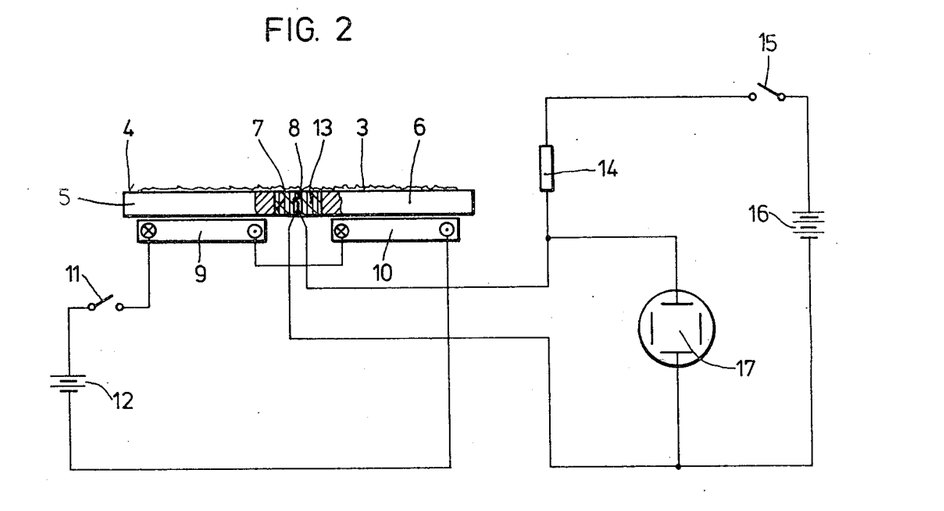
FIG. 2 is a diagrammatic representation of the measuring arrangement in one embodiment of the invention by means of which the temperature curve of FIG. 1 was recorded.

FIG. 2 illustrates a basic measuring arrangement by means of which the temperature of a liquid 3, which wets the upper surface 4 of a chilling arrangement 5, can be visually indicated. Chilling arrangement 5 comprises a metallic cooling plate 6, having in the central area thereof a recess 7 in which a quick-response thermometer probe 8 is embedded, and two series-connected Peltier elements 9 and 10 which can be connected to a voltage source 12 via a switch 11. Elements 9 and 10 are in heat-conductive contact with cooling plate 6, and when switch 11 is closed, a current flows through Peltier elements 9 and 10 in a direction such that plate 6 is chilled. Thermometer probe 8, preferably an NTC resistor, is embedded in a heat-insulating material 13 and is thus heat-insulated relative to the refrigerating zone of cooling plate 6, so that probe 8 really responds only to the temperature of the liquid situated above probe 8 and not to the temperature of the mentioned refrigerating zone.

Thermometer probe 8 is connectible across a resistor 14 and a further switch 15 to a second voltage source 16. The voltage drop occurring at probe 8 is dependent upon the temperature of the liquid situated above probe 8 and is supplied to the vertical deflector plates of a phosphorescent oscillograph 17, indicated symbolically in the drawing. The horizontal deflector plates of oscillograph 17 are connected to a sweep circuit (not shown) which deflects the luminous spot once from left to right during each chilling operation, i.e., during a period of from 30 to 60 seconds, so that curve 2, for example, appears on the screen of oscillograph 17.

Figure 3:
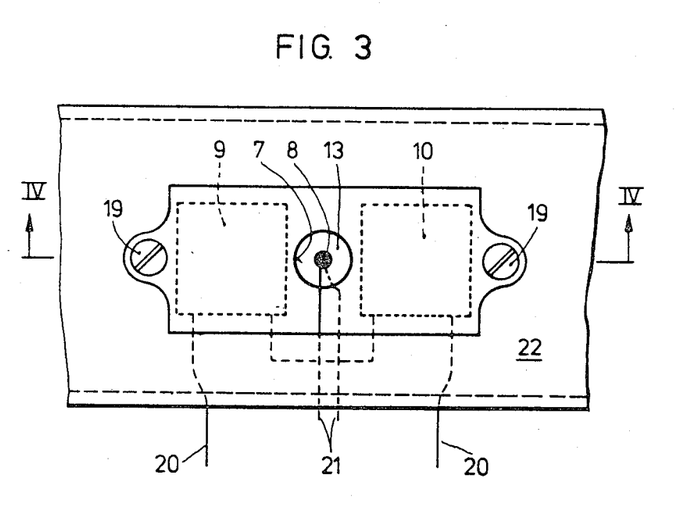
FIG. 3 is a top plan view of part of the chilling arrangement in an embodiment of the invention.
Figure 4:
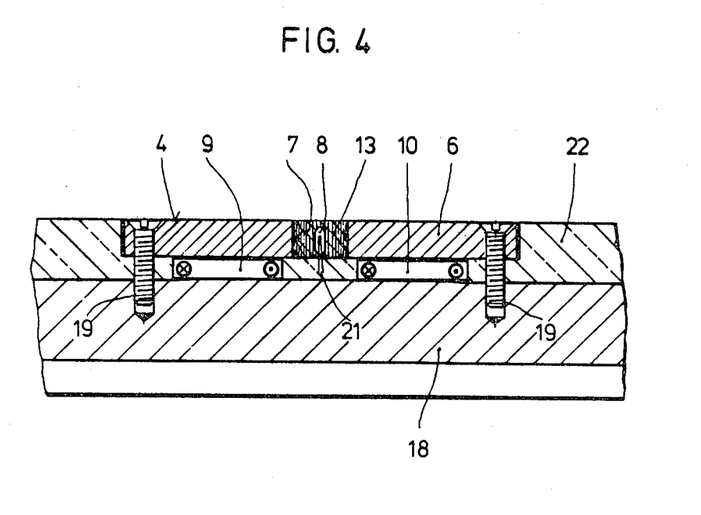
FIG. 4 is a section taken on the line IV—IV of FIG. 3.

FIG. 3 is a top plan view of the chilling arrangement in an embodiment of the invention, while FIG. 4 is a section taken on the line IV—IV of FIG. 3. The chilling device proper comprises cooling plate 6, made of a metal which is a good conductor of heat, e.g., copper, and the two Peltier elements 9 and 10. The faces of elements 9 and 10 which heat up during their operation rest against a cooling block 18, also of a metal which is a good conductor of heat, e.g., copper. Cooling block 18 absorbs the heat withdrawn from the liquid and the dissipated heat of Peltier elements 9 and 10. The faces of elements 9 and 10 which are cooled during their operation rest against cooling plate 6.

In order to ensure good heat transmission between the lower faces of Peltier elements 9 and 10 and cooling block 18, and between the upper faces of those elements and cooling plate 6, elements 9 and 10 are clamped between plate 6 and block 18 by means of two screws 19 securing plate 6 to block 18. In order to prevent the formation of heat bridges, screws 19 are made of plastic. Thermometer probe 8 is embedded in recess 7 by means of heat-insulating plastic material 13 in such a way as to be protected from moisture, and so that the temperature-sensitive portion of probe 8 is situated close to the surface of the plastic material 13, thereby ensuring that this portion responds as quickly as possible to the temperature of the liquid above it.

As may be seen from FIG. 3, Peltier elements 9 and 10 are connected in series, and both the other two connections 20 of the Peltier elements and the two connections 21 of thermometer probe 8 exit laterally. The space between the plane defined by the upper surface 4 of cooling plate 6 and the upper surface of cooling block 18 is filled with a heat-insulating plastic material 22 so that heat is withdrawn by Peltier elements 9 and 10 only from cooling plate 6 insofar as possible.

When the chilling arrangement illustrated in FIGS. 3 and 4 is intended for stationary use, it will be countersunk in the roadway so that upper surface 4 of cooling plate 6 is flush with the road surface and as horizontal as possible. The chilling arrangement is then connected by a four-wire cable to an evaluating device, to be described below, by means of which the freezing point of the liquid on cooling plate 6, hence on the roadway, can be determined. The heat withdrawn from the liquid, and the dissipated heat of Peltier elements 9 and 10, passes into the ground via cooling block 18.

When the chilling arrangement illustrated in FIGS. 3 and 4 is intended for mobile duty, it will be mounted on a monitoring vehicle in such a way that the upper surface 4 of cooling plate 6 is as horizontal as possible and that cooling block 18 is in close, heat-conductive contact with, for instance, the chassis of the vehicle. In order to find out the temperature at which a mixture of salt, mud, and liquid on the road will freeze, a small amount of this mixture is taken up with a pipette or a spoon and placed on cooling plate 6 so that the heat-insulated zone, i.e., the plastic material 13, in the central area of plate 6, and at least the marginal region around central recess 7, are covered by the mixture. Preferably, the mixture is taken up from the roadway with a blotter, and the saturated blotter is then laid on cooling plate 6.

In both stationary and mobile use of the chilling arrangement, the temperature variation during the chilling process of the portion of test liquid situated on plastic material 13 is ascertained by means of thermometer probe 8 and transmitted to the evaluating device now to be described with reference to FIG. 5.

Figure 5:
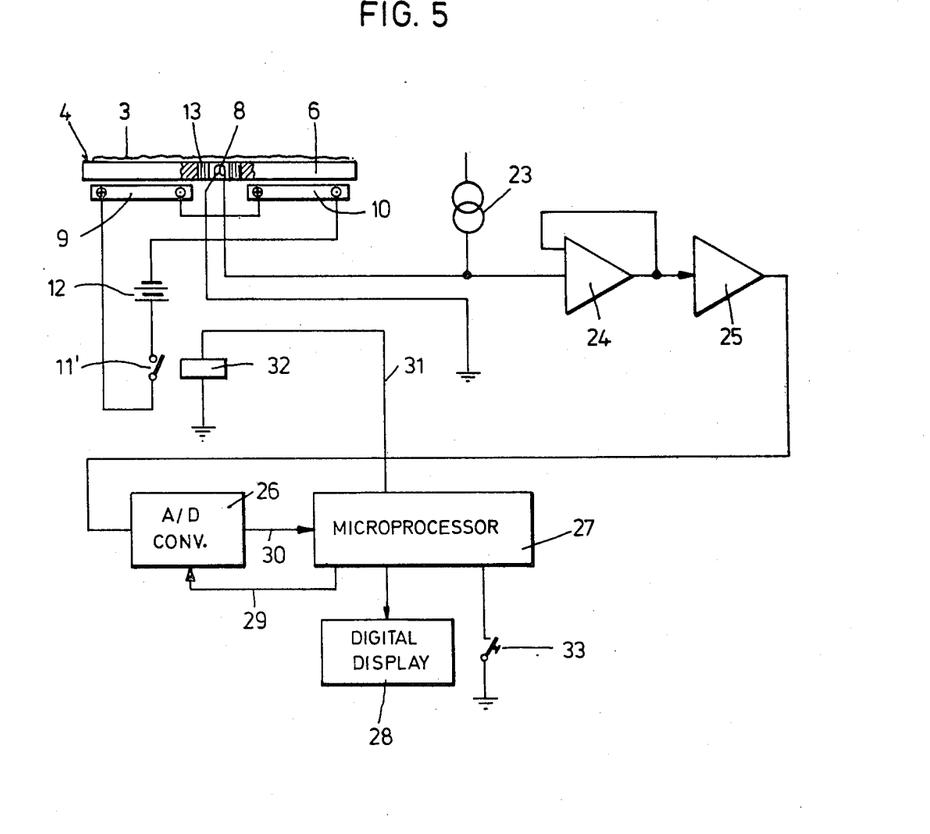
FIG. 5 is a block diagram of another embodiment of the invention.

Instead of the evaluating device shown in FIG. 2, utilizing a long-persistence oscillograph, the evaluating device illustrated in FIG. 5 comprises a constant-current source 23, an impedance transformer 24, a measuring amplifier 25, an analog-to-digital converter 26, a commercially available microprocessor 27, e.g., of the 8748 type, and a digital display 28. Current source 23 is connected in series to thermometer probe 8, which is an NTC resistor. The voltage drop occurring at probe 8, dependent upon the temperature measured, is supplied to the input of impedance transformer 24. The latter controls amplifier 25, which amplifies the signal proportional to the solidification curve to a desired voltage so that this voltage can be converted into a digital signal by A-D converter 26. Via a control line 29, microprocessor 27 periodically transmits orders to A-D converter 26 to sample the analog signal received from amplifier 25, convert it to digital values, and introduce it via a data bus 30 into microprocessor 27 for storage and processing of such digital signals. The data introduced into microprocessor 27 are processed there in a manner to be described below, and the result is visually indicated by means of digital display 28, from which the freezing-point temperature of the liquid on the cooling plate can be read off directly in degrees Celsius. Via another control line 31, a relay 32 having a make contact 11', corresponding to switch 11 of the measuring arrangement illustrated in FIG. 2, is periodically energized by microprocessor 27. Each time this happens, a new chilling operation is initiated inasmuch as contact 11' connects Peltier elements 9 and 10 to voltage source 12.

Figure 6:
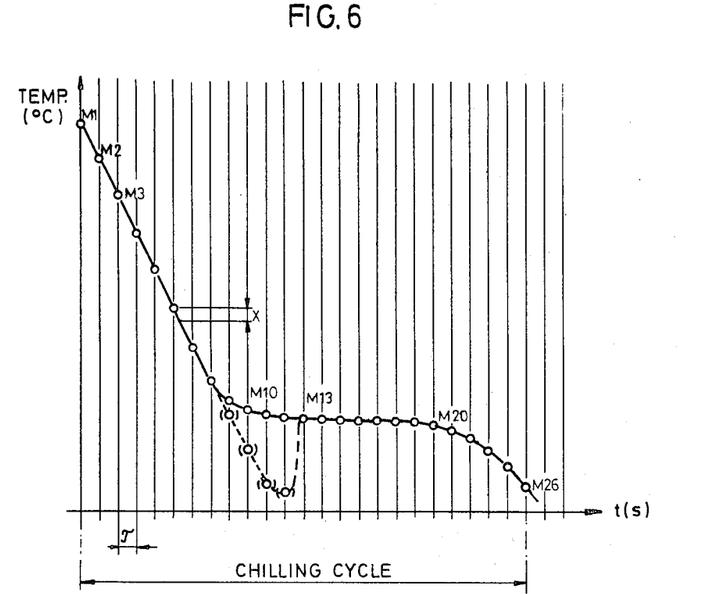
FIG. 6 is a graph showing the sampling process of the temperature curve.
Figure 7:
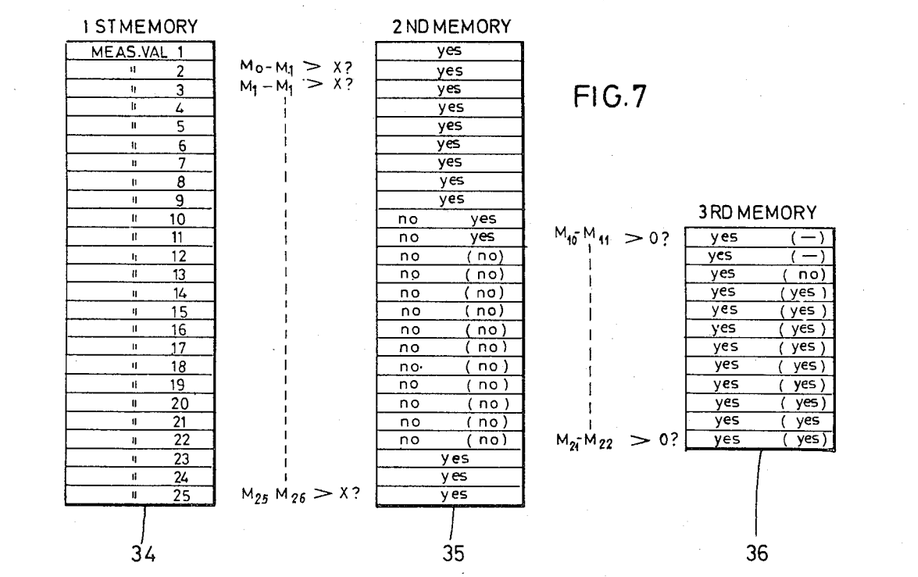
FIG. 7 is a simplified representation of the storage locations of three memories of the microprocessor in the apparatus of FIG. 5.

The mode of operation of the apparatus illustrated in FIG. 5 will now be described with reference to FIGS. 6 and 7. FIG. 6 shows the variation in temperature of the portion of liquid situated above thermometer probe 8 during the chilling process. The voltage at the output of measuring amplifier 25 varies identically. The size of the insulating zone formed by plastic material 13 and the cooling capacity of Peltier elements 9 and 10 are such that within 30 to 60 seconds, the amount of liquid in that zone is frozen solid.

Microprocessor 27 is so programmed that when a start button 33 is pressed, the microprocessor energizes relay 32 via control line 31 and thereby initiates the chilling operation. At the same time, via control line 29, it gives A-D converter 26 the order to convert the first measured value $M_1$ to a digital measurement signal and to supply this signal to microprocessor 27 itself via data bus 30. This order is repeated at regular intervals $\tau$, e.g., every 0.2 seconds, during the whole chilling cycle. In this way, all the measured values (only $M_1$ to $M_{25}$ being shown in FIG. 6 for the sake of simplicity) are introduced into microprocessor 27 in the form of digital measurement signals during the course of a working cycle. After the last digital measurement signal has been introduced into microprocessor 27, relay 32 is de-energized and the chilling cycle terminated.

Measured values $M_1$ to $M_{25}$, represented by small circles in FIG. 6, belong to the solidification curve of a contaminated liquid mixture such as is formed on the surface of a road or street by water in which a thawing agent, e.g., salt, is dissolved and which is mixed with impurities. The measured values represented by small circles in parentheses are those obtained when substantially uncontaminated rainwater is subjected to the chilling process.

Microprocessor 27 contains first, second, and third memories 34, 35 and 36, respectively. These memories are very schematically represented in FIG. 7. Instead of three memories, one large memory with three separate storage zones may be used. First memory 34 comprises at least as many storage locations as are needed to store all the digital measurement signals, corresponding here to measured values $M_1$ to $M_{25}$. All the digital measurement signals supplied to microprocessor 27 via data bus 30 during a chilling cycle are stored in memory 34. For example, if a chilling cycle lasts 50 seconds and the sampling intervals are 0.2 seconds, a total of 250 measured values are stored in memory 34. The relatively short sampling intervals $\tau$ are necessary in order to be sure that no jumps of temperature are missed.

After the second measured value has been fed into memory 34, the difference between the first and second measured values is determined and compared with a predetermined temperature difference x. The result of this comparison, i.e., whether the difference is greater than x or not, is stored in the first storage location of second memory 35, which may be called a marker memory, binary 1 meaning "yes" and binary 0 meaning "no", for example. In the same way, the difference is determined between each further measured value fed into memory 34 and the value introduced immediately before, this difference is compared with the quantity x, and the result is introduced into memory 35. Upon completion of a chilling cycle, all results of the comparisons, i.e., the answers to whether the difference between a preceding measured value $M_n$ and a directly following measured value $M_{n+1}$ is greater than the quantity x or not, are stored in second memory 35. The answers shown in parentheses in memory 35 in FIG. 7 apply to the solidification curve for which the measured values are shown as (o) in FIG. 6. The end of the chilling cycle is fixed by a time-monitoring counter (not shown) which counts the number of orders given to A-D converter 26 and stops the chilling process by causing relay 32 to be de-energized when a pre-settable count is reached—in the simplified case described above, for example, 25.

At the end of the chilling operation, the actual evaluation of measured values $M_1$ to $M_{25}$ stored in first memory 34 is begun.

Figure 8:
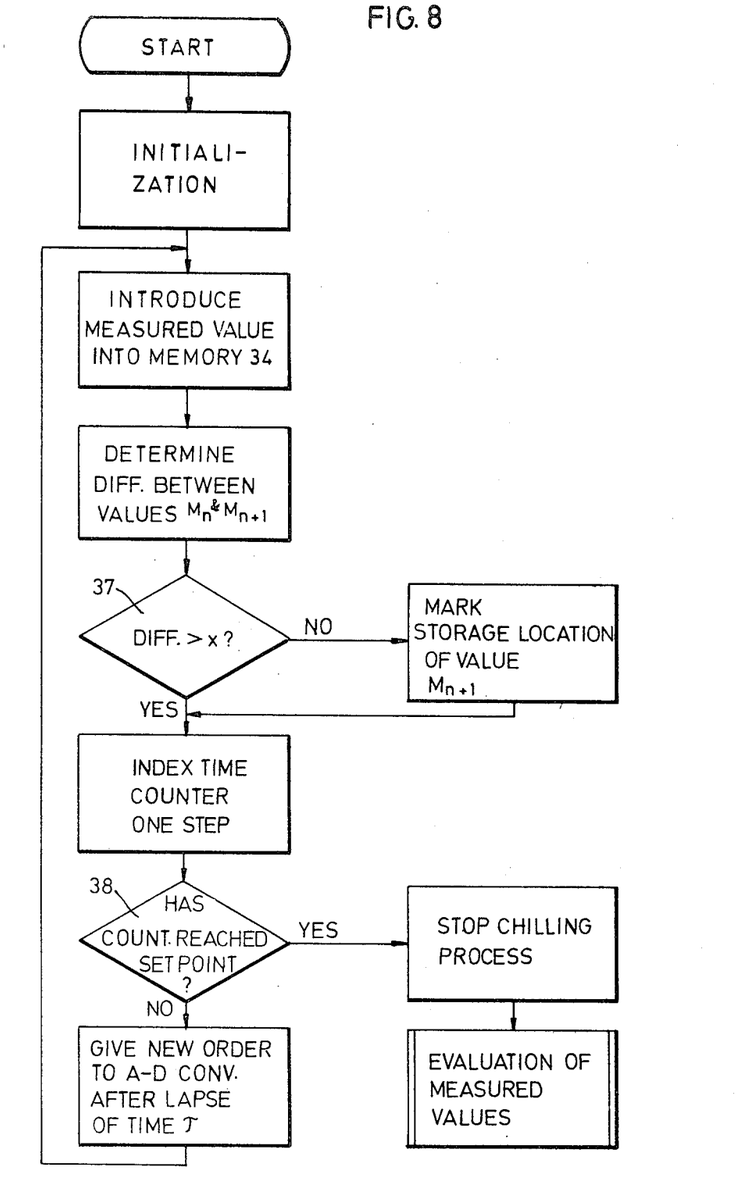
FIG. 8 is a flow chart according to which the apparatus of FIG. 5 operates.

The flow chart in FIG. 8 shows the mode of operation of the apparatus of FIG. 5 for reading in and storing the measured values in first memory 34 and for marking certain such values. After start button 33 has been pressed, initialization takes place, i.e., A-D converter 26 receives the first order to sample the first measured value $M_1$ and to convert the analog value into a digital value which is then supplied to microprocessor 27 via data bus 30 and stored in first memory 34, the time-monitoring counter (not shown) is set to its starting position, the quantity x is set, relay 32 is energized for initiating the chilling process, and after time $\tau$ has elapsed a second order is given to A-D converter 26 to sample the second measured value $M_2$.

After initialization, the second measured value $M_2$ on the data bus is introduced into memory 34. The difference between the first and second measured values is then ascertained. At a decision point 37, it is decided whether this difference is greater than x or not. If it is not, the fact is retained in second memory 35, which marks the storage location of value $M_2$. After marking of the respective storage location, or if it is decided at the decision point that the difference is greater than x, the time-monitoring counter is indexed by one step, and it is checked at a further decision point 38 whether the counter has reached its set point or not. If it has not, a new order is given to A-D converter 26 after time $\tau$ has elapsed, whereby the third measured value $M_3$ is put on data bus 30. The same procedure as described above is then repeated over and over until the count of the time-monitoring counter has reached its set point. When this happens, the chilling process is terminated in that relay 32 is de-energized, and immediately thereafter the evaluation of the measured values stored in first memory 34 and marked by second memory 35 is initiated.

Figure 9:
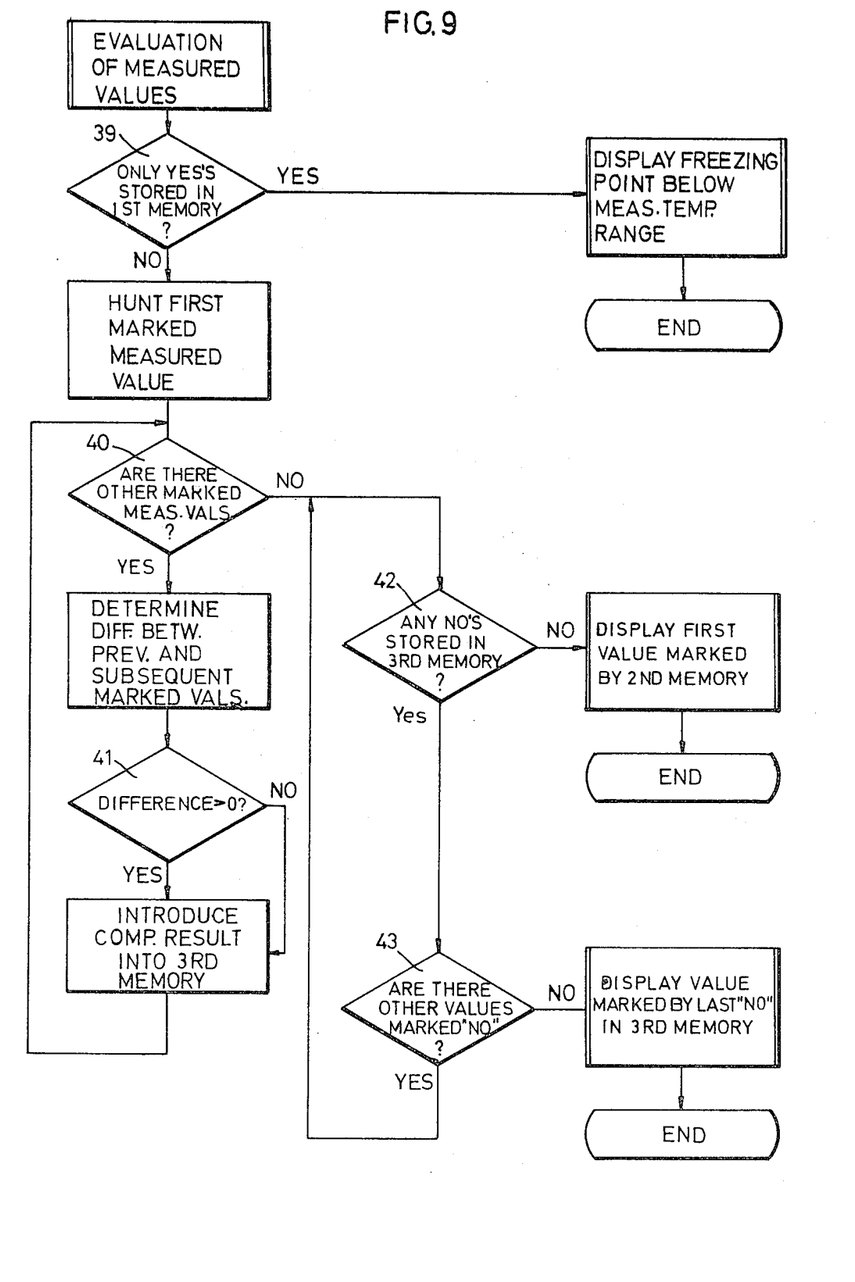
FIG. 9 is a further flow chart.

The evaluation operation may be seen from the flow chart in FIG. 9. At a decision point 39, it is checked whether only "yes" responses are stored in memory 35. If so, this means that the freezing point of the liquid tested is below the temperature range examined. For instance, if the chilling arrangement is designed to chill the liquid to $-15°$ C. and if a "yes" is stored at every storage location in memory 35, this means that the freezing point of the liquid is below $-15°$ C. This fact can be indicated by the flashing of one or more symbols of display device 28. After such a display, both the chilling operation and the evaluation of the measured data are ended.

If it is ascertained at decision point 39 that not only "yes" responses are stored in memory 35, a search for the first measured value in the marked storage zone of memory 34 is thereby initiated. At a decision point 40, it is checked whether still other storage locations in first memory 34 have been marked by second memory 35. If so, the difference between the previous marked value and the subsequent one is ascertained. At a further decision point 41, it is decided whether this difference is greater than 0. The result of the comparison, "yes" or "no", is stored in third memory 36. It is then checked again at decision point 40 whether there are any further marked storage locations. This procedure continues to be repeated until it is ascertained at decision point 40 that there are no further marked storage locations. It is thereupon checked at a decision point 42 whether any "no" responses are stored in third memory 36. If not, the display of the first measured value marked by second memory 35 is initiated. In FIG. 6, this first marked value is the first one, $M_{10}$, in the substantially horizontal portion of the solid-line curve and simultaneously the freezing point of the liquid tested. Upon display of the freezing point, both the chilling operation and the evaluation are ended.

If it is found at decision point 42 that there is a "no" stored in third memory 36, it is checked at a further decision point 43 whether still other "no" responses are stored there. If not, the measured value marked by this "no" is read out of first memory 34 and displayed. In the temperature curve formed by the measured values (o) in FIG. 6, the one marked by the "no" in memory 36 is measured value $M_{13}$, which is displayed as the freezing point. This ends the chilling process and the evaluation.

If it is found at decision point 43 that memory 36 contains further "no" responses, the check continues until no more such responses are found stored in that memory. Several "no" responses may be stored in memory 36 if the temperature does not rise abruptly but gradually after undercooling. The measured value marked by the last "no" in memory 36 is read out of memory 34 and displayed as the freezing point. The chilling process and evaluation are thus ended.

Microprocessor 27 may be programmed to initiate a chilling operation and effect an evaluation approximately every 10 minutes.

The flow chart described above with reference to FIG. 9 is but one of several possibilities of evaluating the shape of the solidification curve with the aid of microprocessor 27 and digitally indicating the freezing point.

What is claimed is:
1. Apparatus for determining the freezing point of a liquid lying on or taken from a roadway, of the type having chilling means and a thermometer probe for measuring the temperature of the liquid, wherein the improvement comprises:
   a heat-conductive plate having a surface for contacting the liquid a recess in the central area thereof,
   means for heat-conductively connecting said plate to said chilling means, a heat-insulating material disposed in said recess, said
thermometer probe being embedded in said material, circuit means connected to said thermometer probe for establishing a temperature difference on the basis of repeated temperature measurements and for evaluating said temperature difference to determine said freezing point, and display means for displaying said freezing point.

2. The apparatus of claim 1, wherein said chilling means comprise one or more Peltier elements, said apparatus further comprising a cooling block and means for applying a voltage to said Peltier elements, said Peltier elements being disposed between said plate and said cooling block with the faces of said Peltier elements intended to heat up upon application of said voltage resting against said cooling block.

3. The apparatus of claim 2, further comprising one or more plastic screws securing said plate to said cooling block, a heat-insulating material being disposed in a space adjacent to said plate and said Peltier elements bounded by said cooling block and by the plane defined by the surface of said plate remote from said Peltier elements.

4. Apparatus as in any one of claims 1–3, wherein said circuit means comprise a measuring amplifier, an analog-to-digital converter, and a microprocessor.

5. The apparatus of claim 4, wherein said microprocessor includes a first memory for storing a plurality of sampling values of the temperature of said liquid during chilling thereof, a second memory for storing the results of a check as to whether the difference between each two successive said sampling values exceeds a predetermined value or not, and a third memory for storing the results of a further check as to whether any said difference which does not exceed said predetermined value also does not exceed zero.

6. The apparatus of claim 5, wherein said microprocessor is programmed to initiate a chilling operation and effect an evaluation approximately every 10 minutes.

7. The apparatus of claim 5, further comprising a manually-operated starting means.

* * * * *